United States Patent
Lin et al.

(10) Patent No.: US 11,220,495 B2
(45) Date of Patent: Jan. 11, 2022

(54) COMPOUND OF 3,3,3',3'-TETRAMETHYL-1,1'-SPIROBIIN-DANE-BASED BISOXAZOLINE LIGAND, INTERMEDIATE THEREOF, PREPARATION METHOD THEREOF AND USE THEREOF

(71) Applicant: ZHEJIANG UNIVERSITY, Hangzhou (CN)

(72) Inventors: Xufeng Lin, Hangzhou (CN); Haorui Gu, Hangzhou (CN); Weiye Sun, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 80 days.

(21) Appl. No.: 16/955,062

(22) PCT Filed: Dec. 29, 2017

(86) PCT No.: PCT/CN2017/119944
§ 371 (c)(1),
(2) Date: Jun. 18, 2020

(87) PCT Pub. No.: WO2019/119516
PCT Pub. Date: Jun. 27, 2019

(65) Prior Publication Data
US 2021/0363135 A1    Nov. 25, 2021

(30) Foreign Application Priority Data
Dec. 22, 2017 (CN) .......................... 201711405090.2

(51) Int. Cl.
C07D 413/10 (2006.01)
(52) U.S. Cl.
CPC ........ C07D 413/10 (2013.01); *C07B 2200/07* (2013.01); *C07B 2200/13* (2013.01)
(58) Field of Classification Search
CPC .................................................. C07D 413/10
USPC ....................................................... 548/239
See application file for complete search history.

(56) References Cited

FOREIGN PATENT DOCUMENTS

| CN | 101412738 A | | 4/2009 | |
|----|-------------|---|--------|---|
| CN | 101560191 A | | 10/2009 | |
| CN | 101565434 A | * | 10/2009 | .......... C07F 15/0046 |
| CN | 101671313 A | | 3/2010 | |

OTHER PUBLICATIONS

International Search Report (PCT/CN2017/119944); dated Sep. 13, 2018.

Synthesis and characterization of new organic phosphonates monomers as flame retardant additives for polymers; Oct. 24, 2014.
Highly Enantioselective Insertion of Carbenoids into N—H Bonds Catalyzed by Copper Complexes of Chiral Spiro Bisoxazolines; Feb. 17, 2007.

* cited by examiner

*Primary Examiner* — Kahsay Habte
(74) *Attorney, Agent, or Firm* — W&G Law Group

(57) ABSTRACT

Provided are a compound of 3,3,3',3'-tetramethyl-1,1'-spirobiindane-based bisoxazoline ligand, an intermediate, a preparation method and uses thereof. The compound of bisoxazoline ligand is a compound having a structure represented by formula I, or an enantiomer, a raceme, or diastereomer thereof. The bisoxazoline ligand can be prepared via a preparation scheme in which the cheap and easily available 6,6'-dihydroxyl-3,3,3',3'-tetramethyl-1,1'-spirobiindane is used as a starting raw material and the compound represented by formula II serves as the key intermediate through a series of reactions. The new bisoxazoline ligand developed by the present application can be used in catalytic organic reaction, in particular as a chiral bisoxazoline ligand that is widely used in many asymmetric catalytic reactions of metal catalysis, and thus it has economic practicability and industrial application prospect.

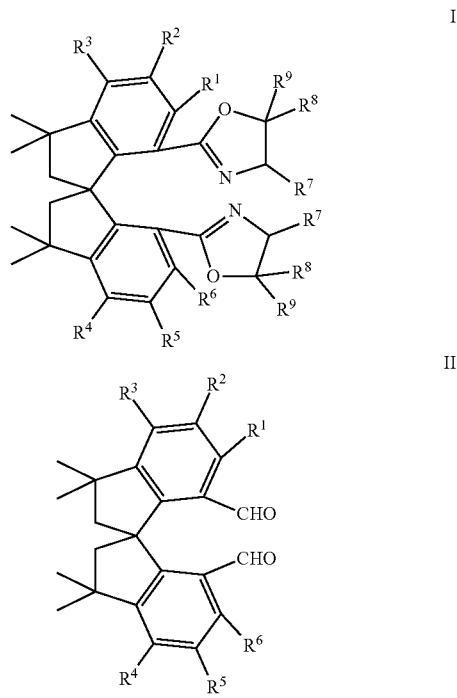

3 Claims, 1 Drawing Sheet

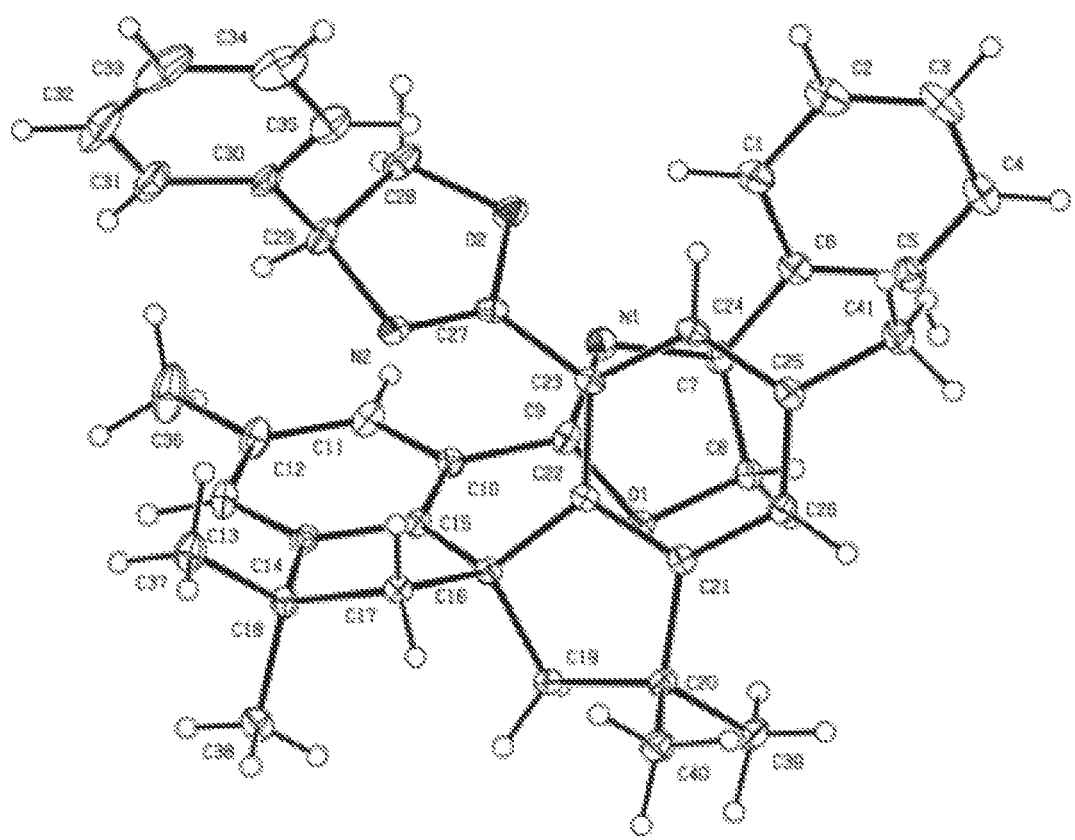

COMPOUND OF 3,3,3',3'-TETRAMETHYL-1,1'-SPIROBIINDANE-BASED BISOXAZOLINE LIGAND, INTERMEDIATE THEREOF, PREPARATION METHOD THEREOF AND USE THEREOF

TECHNICAL FIELD

The present application relates to the technical field of organic chemistry, and relates to a novel compound of 3,3,3',3'-tetramethyl-1,1'-spirobiindane-based bisoxazoline ligand, an intermediate, a preparation method and a use of the ligand compound. The ligand can be used in a coupling reaction or an asymmetric catalytic reaction.

BACKGROUND

Asymmetric catalytic synthesis is currently one of the most active research fields in chemical science. It is the most direct and effective method to obtain optically active molecules. It has advantage of chiral proliferation, high enantioselectivity, economic efficiency, and convenience of industrialization. It is a challenging topic in the field of synthetic chemistry to achieve asymmetric catalytic synthesis reactions with high-efficiency and high-selectivity, and one of the pivotal scientific issues is to develop and discover new highly effective chiral ligands and their catalysts. The design and synthesis of chiral ligands have been rapidly developed, and many excellent chiral bisoxazoline ligands have been synthesized as follows, some of which have been adopted in the industrial production. However, none of the chiral ligands is for all-purpose due to the existing problems such as limited application scopes for the ligands and high dependence on reaction substrates. Therefore, it is urgent for the catalytic asymmetric synthesis reactions to seek for chiral ligands having new skeletons.

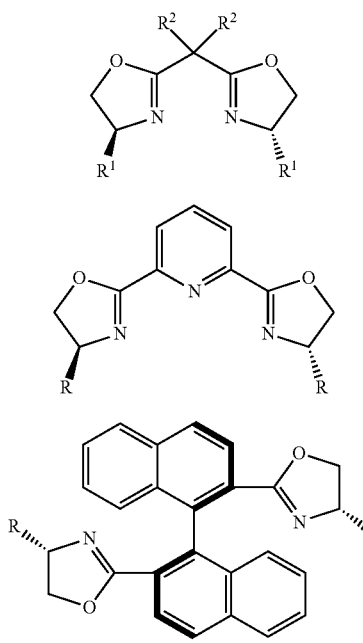

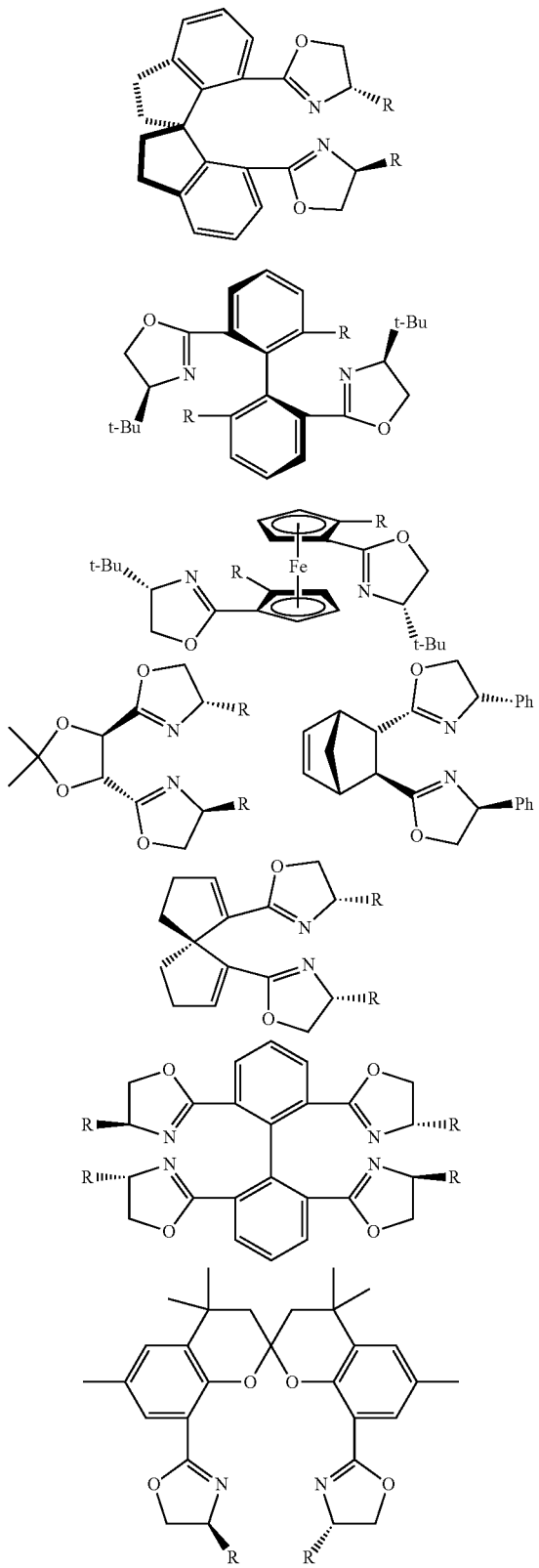

The synthesis design of chiral ligands (for improving catalytic activity and enantioselectivity) follows certain rules, mainly considering electrical and structural factors such as dihedral angle, steric hindrance and skeleton rigidity, etc. It is currently believed that the dihedral angle has a significant influence on the enantioselectivity of asymmetric catalysis (e.g., the literature of *Acc. Chem. Res.* 2007, 40, 1385-1393; *Tetrahedron: Asymmetry;* 15 (2004) 2185-2188; *J. Org. Chem.* 1999, 65, 6223).

In 1999, Birman el al. synthesized and obtained racemic 1,1'-spirobiindane-7,7'-diol SPINOL from m-methoxybenzaldehyde via a six-step reaction, and obtained the corresponding optical enantiomer through chemical resolution (*Tetrahedron: Asymmetry* 1999, 10, 12), and it indicated that the compound may be used to synthesize various chiral ligands However, according to such a scheme or other-published methods, it is obviously impossible to obtain the corresponding 3,3,3',3'-tetramethyl-1,1'-spirobiindane-7,7'-diol. In 2003, using the optically active 1,1'-spirobiindane-7,7'-diol SPINOL, as a raw material, Zhour Qilin et al. synthesized a 1,1'-spirobiindane-based bisoxazoline ligand SpiroBOX (*Tetrahedron: Asymmetry* 17 (2006) 634, CN101565434, CN100432083) through a five-step reaction, which was successfully used in the catalytic asymmetric reaction. However, starting from the industrially available raw material m-methoxybenzaldehyde, the corresponding SpiroBOX was obtained through at least 11 steps of synthesis reaction and 1 step of chiral resolution, which has lengthy reaction steps, increased costs, and influenced practicability.

6,6'-dihydroxyl-3,3,3',3'-tetramethyl-1,1'-spirobiindane (MSPINOL) could be obtained with high yields through acid catalysis directly from industrialized bisphenol series products, and large-scale preparation methods and chiral resolution methods were subsequently reported (referring to the following reaction equation, *J. Chem. Soc.,* 1962, 415-418; *Org Lett.,* 2004, 6, 2341-2343; US 2006/0020150; U.S. Pat. No. 4,879,421; *Bull. Chem. Soc. Japan,* 1977, 44, 496-505; Chinese patent for invention, with a filing No. of CN 201711330428.2):

reaction of acetone and phenol or its derivatives. In addition, many industrial bisphenol series products (bisphenol A, bisphenol C, etc.) are available and on large-scale sales, for example, the annually produced and sold bisphenol A in the world are as high as more than 3 million tons, with a price less than 10,000 RMB per ton. The present application is intended to utilize cheap and easily available 3,3,3',3'-tetramethyl spirobiindane-6,6'-diphenol to design and prepare the corresponding 3,3,3',3'-tetramethyl-1,1'-spirobiindane-based oxazoline ligand. Compared with 1,1'-spirobiindane-based oxazoline ligand, such a kind of ligands has no active aryl methylene group on the spiro ring skeleton, the 3,3,3',3'-tetramethyl-1,1'-spirobiindane skeleton is more stable and has stronger rigidity, the raw materials thereof are cheap and abundant, the synthesis scheme is shorter, the preparation cost is low, the practicability is high, and the unique dihedral angle indicates different catalytic effects or uses. Based on the method disclosed in the present application, the 3,3,3',3'-tetramethyl-1,1'-spirobiindane-based bisoxazoline ligand is generally prepared with the industrial large-tonnage raw material bisphenol via a seven-step synthesis reaction scheme. Most of the post-treatments are simple and easy to scale up (the following reaction formula is taken as an example). 3,3,3',3'-tetramethyl-1,1'-spirobiindane-based bisoxazoline ligands MSpiroBOX with different structures can be prepared by a two-step reaction from the intermediate tetramethyl spirocyclodicarboxylic acid.

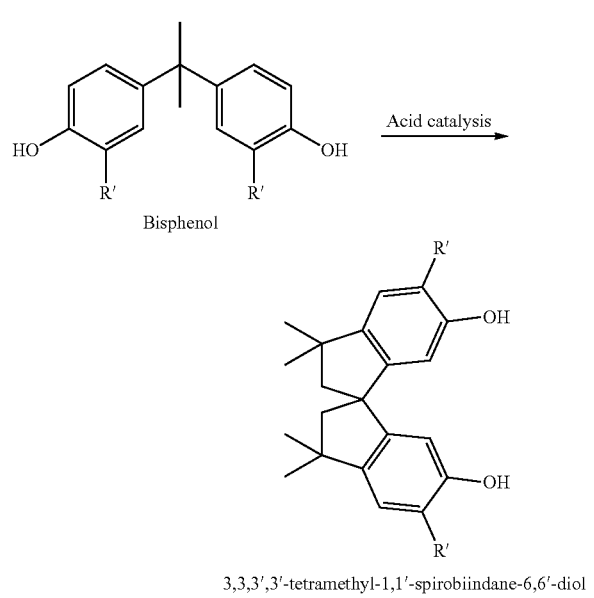

3,3,3',3'-tetramethyl-1,1'-spirobiindane-6,6'-diol 3,3,3',3'-tetramethyl spirobiindane-6,6'-diphenol MSPINOL and its derivatives are known to be mainly used for preparing polymers. The corresponding raw material, bisphenol, is very cheap and can be prepared by condensation

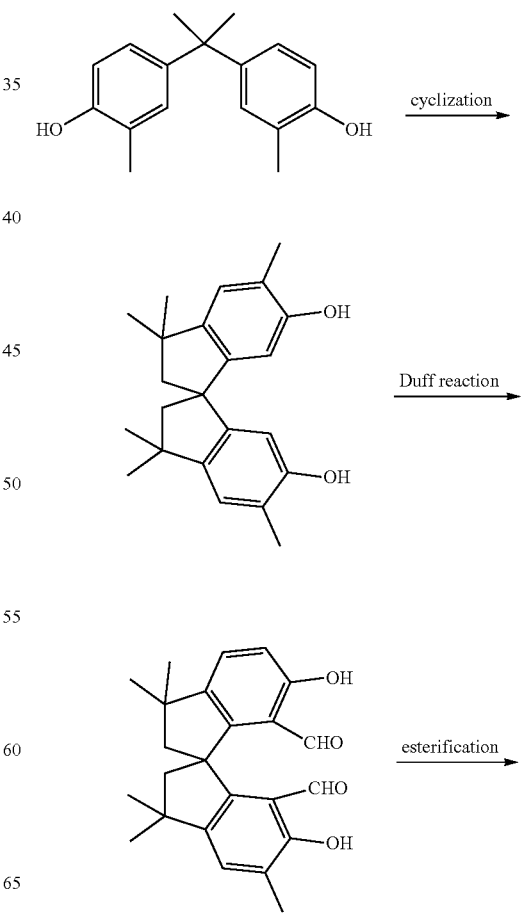

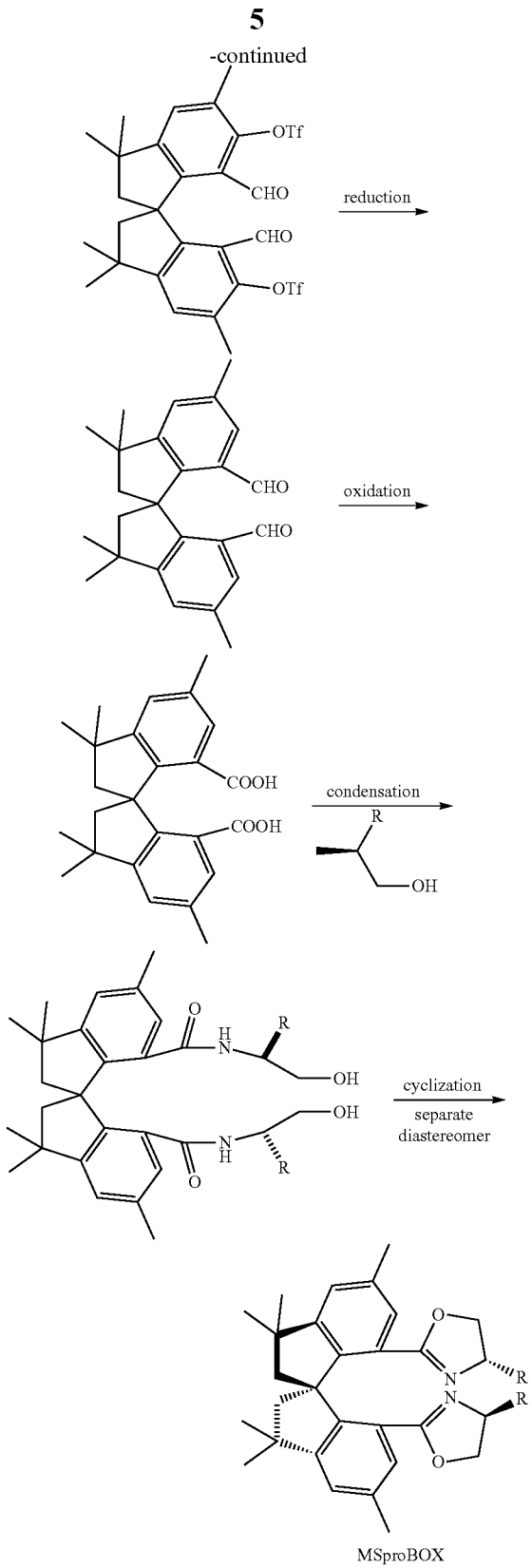

MSproBOX

SUMMARY

The objective of the present application is to provide a novel compound of 3,3,3',3'-tetramethyl-1,1'-spirobiindane-based bisoxazoline ligand, an intermediate, a preparation method and a use of the ligand compound.

A 3,3,3',3'-tetramethyl-1,1'-spirobiindane-based bisoxazoline ligand, being a compound represented by formula I or being an enantiomer, a raceme or a diastereomer thereof:

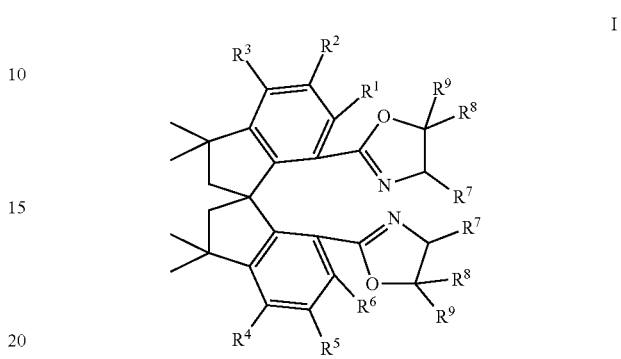

I wherein $R^1$ and $R^6$ are each independently selected from the group consisting of hydrogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted arylmethylenoxy, unsubstituted or substituted heteroarylmethylenoxy, unsubstituted or substituted aryl, and unsubstituted or substituted heteroaryl; $R^2$, $R^3$, $R^4$, and $R^5$ are each independently selected from the group consisting of hydrogen, halogen, $C_1$-$C_{10}$ alkyl or perfluoroalkyl, $C_3$-$C_0$ cycloalkyl, $C_1$-$C_4$ alkoxy or perfluoroalkoxy, unsubstituted or substituted aryloxy, unsubstituted or substituted heteroaryloxy, unsubstituted or substituted aryl, and unsubstituted or substituted heteroaryl; and $R^7$ is selected from the group consisting of $C_1$-$C_{10}$ alkyl or perfluoroalkyl, $C_3$-$C_6$ cycloalkyl, adamantly, ferrocenyl, $C_6$-$C_{14}$ aryl, arylmethylene, heteroarylmethylene, arylethyl, substituted aryl, $C_5$-$C_{14}$ heteroaryl, and substituted heteroaryl, hydroxymethyl, alkylbenzoyloxymethylene, arylbenzoyloxymethylene, CH(Me)OH, CH(Me)OCOPh, CMe$_2$OSiMe$_3$, CMe$_2$OBn, CH$_2$OSiMe$_2$$^t$Bu, CH$_2$SMe, CH$_2$SPh, CH$_2$CH$_2$SMe, CMe$_2$SMe, CMe$_2$Ph, CMePh$_2$, CPh$_3$, CH(Ph)OH, CH(Ph)OMe, CH(Ph)OBn, CH(Ph)OCOMe, CH(Ph)OCOPh, alkoxymethylene, aryloxymethylene; $R^7$ and $R^8$ are each independently selected from the group consisting of hydrogen, $C_1$-$C_{10}$ alkyl or perfluoroalkyl, $C_3$-$C_6$ cycloalkyl, $C_6$-$C_{14}$ aryl, substituted aryl, $C_5$-$C_{14}$ heteroaryl, substituted heteroaryl, alkoxymethylene, aryloxymethylene, CH$_2$OCHPh$_2$, CH$_2$OCPh$_3$ and CH$_2$OCH$_2$Ph; $R^7$ and $R^8$ are capable of forming a ring structure or a benzo ring structure; wherein the substituted aryloxy, the substituted aryl or the substituted heteroaryl contains one or more substituents independently selected from the group consisting of halogen, hydroxyl, N-dimethylamino, $C_1$-$C_4$ alkyl or perfluoroalkyl, $C_3$-$C_6$ cycloalkyl, $C_1$-$C_4$ alkoxy or perfluoroalkoxy, methylenedioxy, $C_6$-$C_{14}$ aryl, aryloxy, and heteroaryl; and the heteroaryl is $C_5$-$C_{14}$ heteroaryl.

An intermediate compound for preparing the 3,3,3',3'-tetramethyl-1,1'-spirobiindane-based bisoxazoline ligand is a compound represented by formula II, or being an enantiomer, a raceme or a diastereomer thereof:

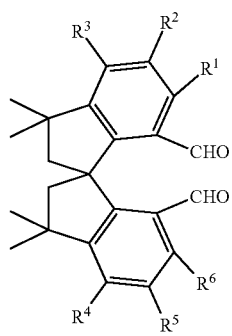

II wherein $R^1$ and $R^6$ are each independently selected from the group consisting of hydrogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted arylmethylenoxy, unsubstituted or substituted heteroarylmethylenoxy, unsubstituted or substituted aryl, and unsubstituted or substituted heteroaryl; $R^2$, $R^3$, $R^4$, and $R^5$ are each independently selected from the group consisting of hydrogen, halogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted aryl, and unsubstituted or substituted heteroaryl; wherein the substituted aryloxy, the substituted aryl or the substituted heteroaryl contains one or more substituents independently selected from the group consisting of halogen, hydroxyl, N-dimethylamino, $C_1$-$C_4$ alkyl or perfluoroalkyl, $C_3$-$C_6$ cycloalkyl, $C_1$-$C_4$ alkoxy or perfluoroalkoxy, methylenedioxy, $C_6$-$C_{14}$ aryl, aryloxy, and heteroaryl; and the heteroaryl is $C_5$-$C_{14}$ heteroaryl; when $R^2$ and $R^5$ are both hydrogen, $R^6$ and $R^1$ may be hydroxyl.

The compound represented by formula I is any one of the following compounds:

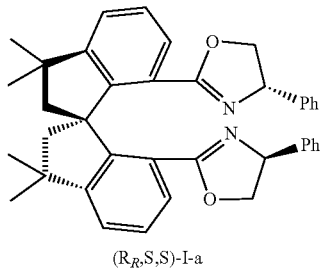

($R_R$,S,S)-I-a

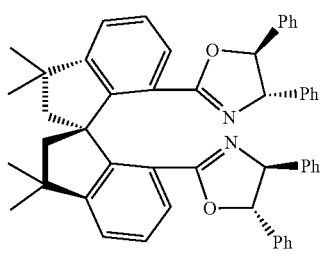

(S,S,$S_R$,S,S)-I-b

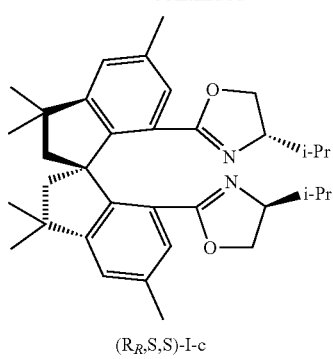

($R_R$,S,S)-I-c

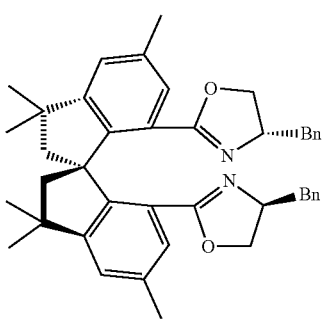

($S_R$,S,S)-I-d

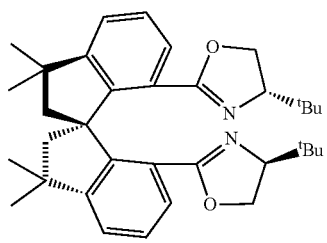

($R_R$,S,S)-I-e

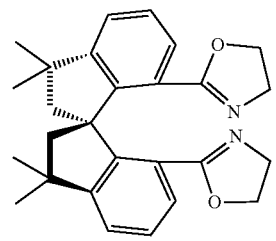

($S_R$)-I-f

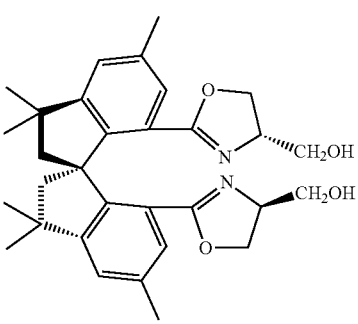

($R_R$,S,S)-I-g

-continued
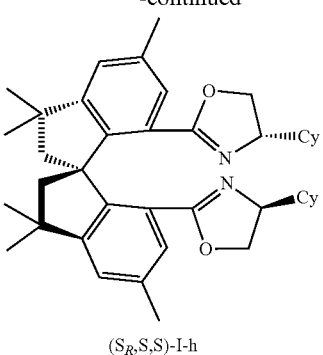
($S_R$,S,S)-I-h
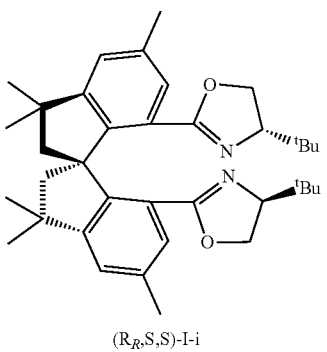
($R_R$,S,S)-I-i
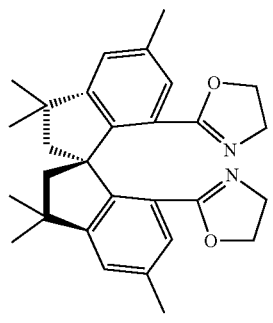
($S_R$)-I-j
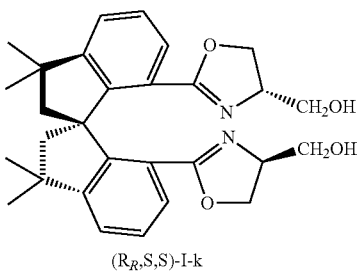
($R_R$,S,S)-I-k
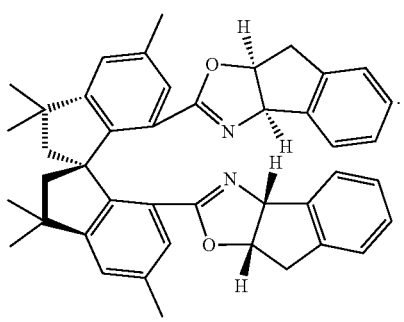
(R,S,$S_R$,R,S)-I-l
The compound represented by formula II is any one of the following compounds:
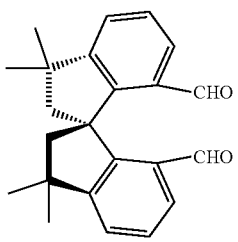
II-a
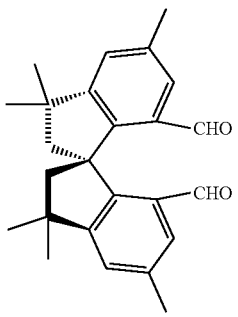
II-b
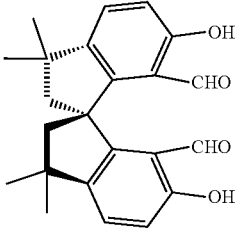
II-c
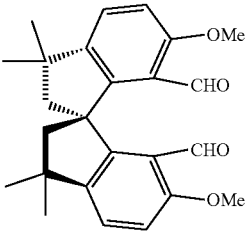
II-d 11
-continued II-e

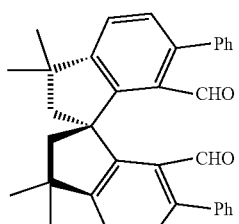

II-f

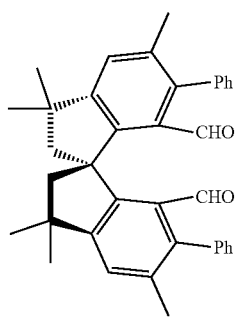

II-g

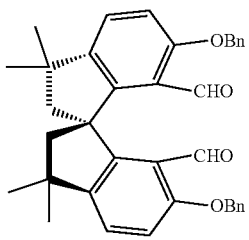

12
-continued

II-h

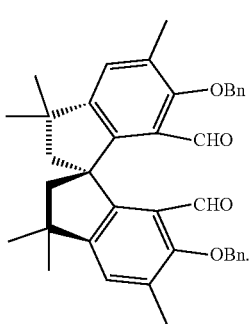

A method for preparing the intermediate compound as represented by formula II, comprising the following steps of: using 6,6'-dihydroxyl-3,3,3',3'-tetramethyl-1,1'-spirobi-indane (formula I) as starting material, and preparing a compound 2 through a Duff reaction (when $R^2$ and $R^5$ are not hydrogen), or through tert-butylation followed by a Duff reaction and a de-tert-butylation (when at least one of $R^2$ and $R^5$ is hydrogen); preparing the compound represented by formula II through an etherification reaction of the compound 2, or firstly preparing a compound 3 by esterifying the compound 2 with trifluoromethanesulfonic anhydride and then preparing the compound represented by formula II through a palladium-catalyzed coupling reaction, or preparing a compound of ester formula II through a reduction reaction of the ester 3:

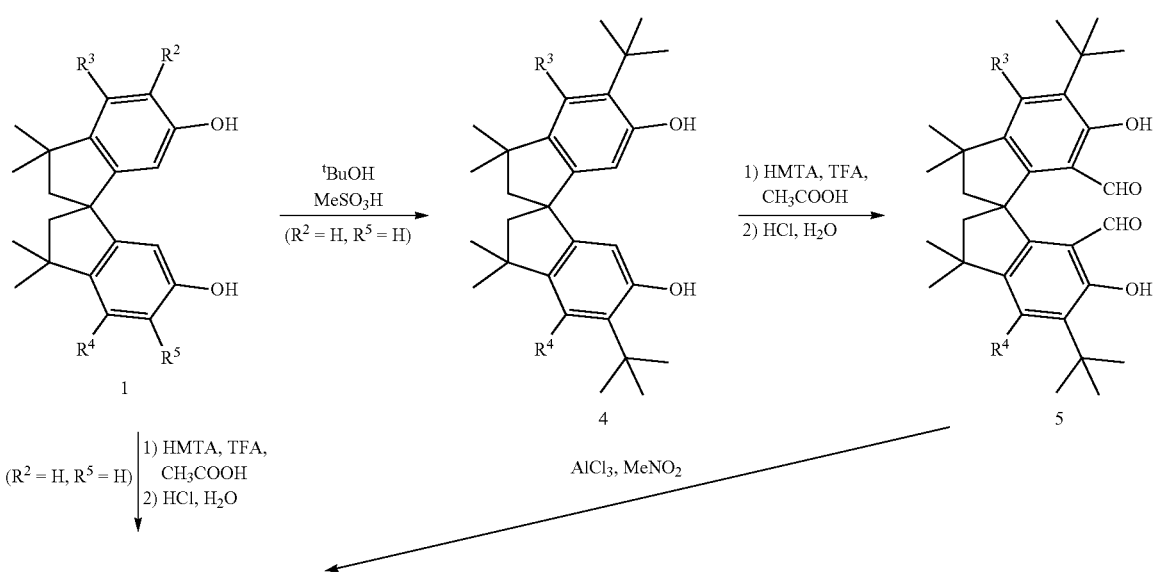

-continued

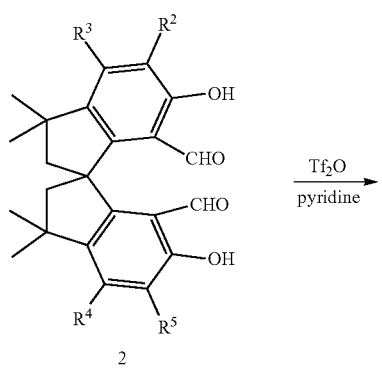 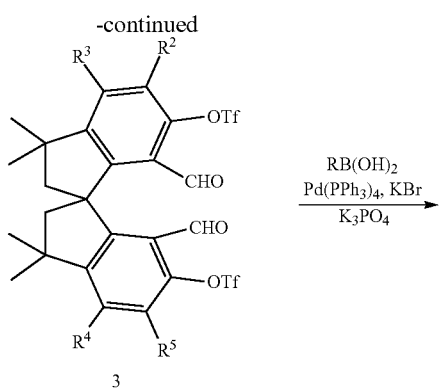 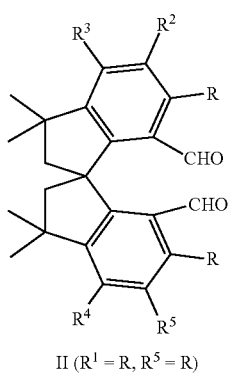

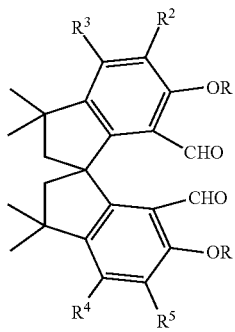 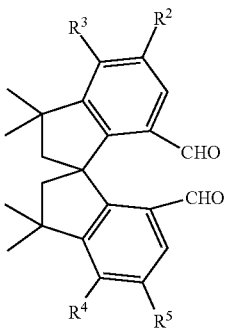

$R^1$-$R^6$ in formulas 1, 2, 3, 4 and 5 are the same as those defined in formula. II, R is selected from the group consisting of $C_1$-$C_{10}$ alkyl or perfluoroalkyl, $C_3$-$C_6$ cycloalkyl, unsubstituted or substituted aryl, and unsubstituted or substituted heteroaryl, and wherein the substituted aryl or the substituted heteroaryl contains one or more substituents independently selected from the group consisting of halogen, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl; and the heteroaryl is $C_5$-$C_{14}$ heteroaryl; HMTA is hexamethylenetetramine and TFA is trifluoroacetic acid.

The method for preparing the compound of formula I, comprising the following steps of using the compound of formula II as a starting material, preparing the compound of formula III through a potassium permanganate oxidation reaction, then carrying out an acyl chlorination reaction, condensing with aminoethanol compounds to form amide alcohol, and finally cyclizing to obtain the compound of formula I:

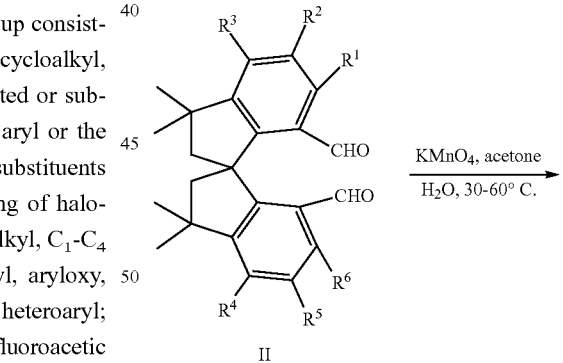

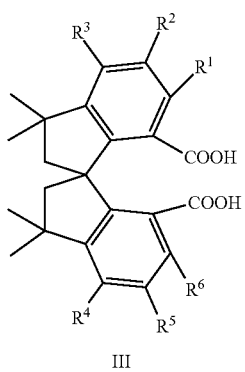

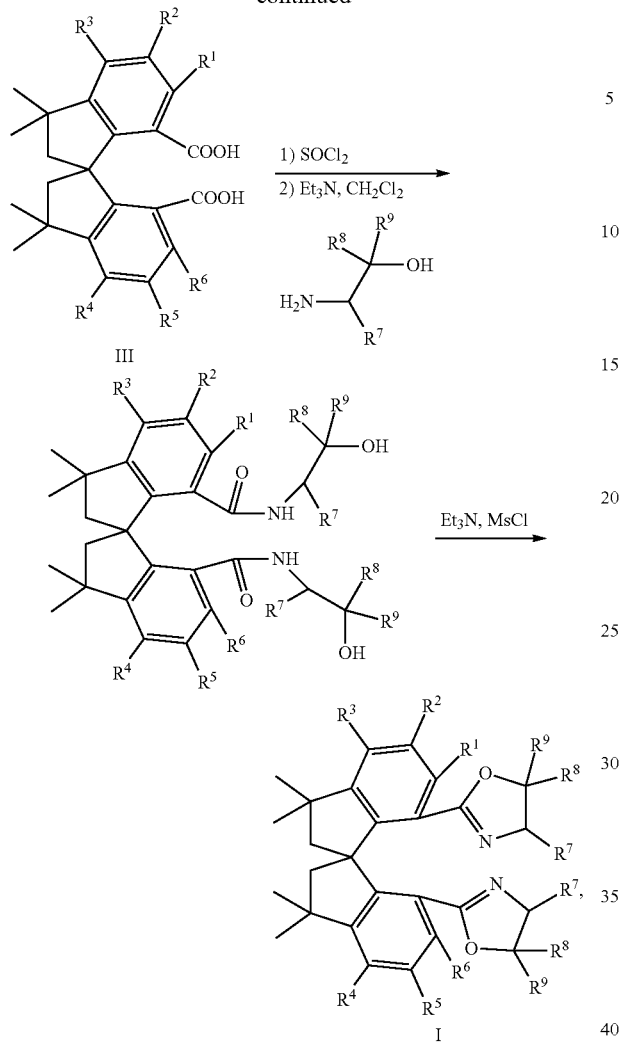

in which $R^1$-$R^9$ are the same as those defined in formula I.

A use of the 3,3,3',3'-tetramethyl-1,1'-spirobiindane-based bisoxazoline ligand, wherein the bisoxazoline ligand is complexed with a metal salt of iron, gold, silver, copper, zinc, magnesium, rhodium, ruthenium, nickel, molybdenum, palladium or cobalt, to prepare a catalyst.

The bisoxazoline ligand may be used in a metal-catalyzed coupling reaction, an insertion reaction, and an asymmetric reaction; the bisoxazoline ligand is preferably used in an asymmetric metal-catalyzed Friedel-Crafts alkylation reaction, an asymmetric N—H, O—H, S—H, Si—H or C—H insertion reaction.

The bisoxazoline ligand of the present application is obtained through a preparation scheme, in which the cheap and easily available 6,6'-dihydroxyl-3,3,3',3'-tetramethyl-1,1'-spirobiindane is used as a raw material. The synthetic route is simple and easy to be applied in large scale.

The new bisoxazoline ligand developed in the present application can be used in the catalytic organic reaction, and particularly, serves as a chiral bisoxazoline ligand that is widely used in many metal-catalyzed asymmetric reactions, and thus it has economic practicability and industrial application prospect.

It should be understood that, within the scope of the present application, the above-mentioned various technical features of the present application and various technical features specifically described in the following examples can be combined with one another to constitute new or preferred technical solutions, which will not described in detail for the sake of brevity.

BRIEF DESCRIPTION OF DRAWINGS

FIG. 1 is an X-ray crystal diffraction pattern of a product ($R_a$, S, S)-I-Ph in Example 1 of the present application.

DESCRIPTION OF EMBODIMENTS

The following examples are provided to facilitating the understanding of the present application, but are not intended to limit to the present application.

General reaction conditions are described as below: when using air-sensitive reagents, all reactions and controls are performed in a nitrogen-filled glove box or using standard Schlenk technology. The reaction solvents are dried by a general standard process.

Example 1

Synthesis of 3,3,5,3',3',5'-hexamethyl-1,1'-spirobiindane-7,7'-dicarboxaldehyde (II-b) and 3,3,5,3',3',5'-hexamethyl-1,1'-spirobiindane-7,7'-dicarboxylic Acid (III-b)

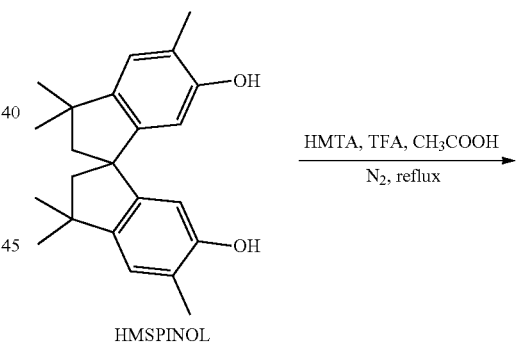

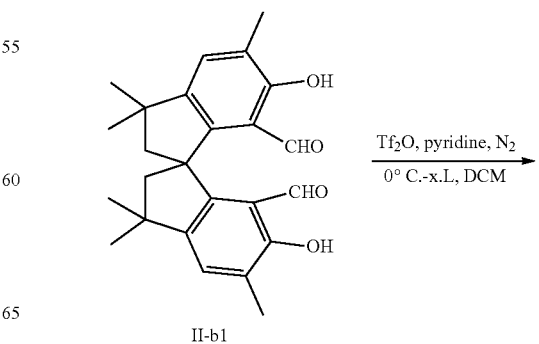

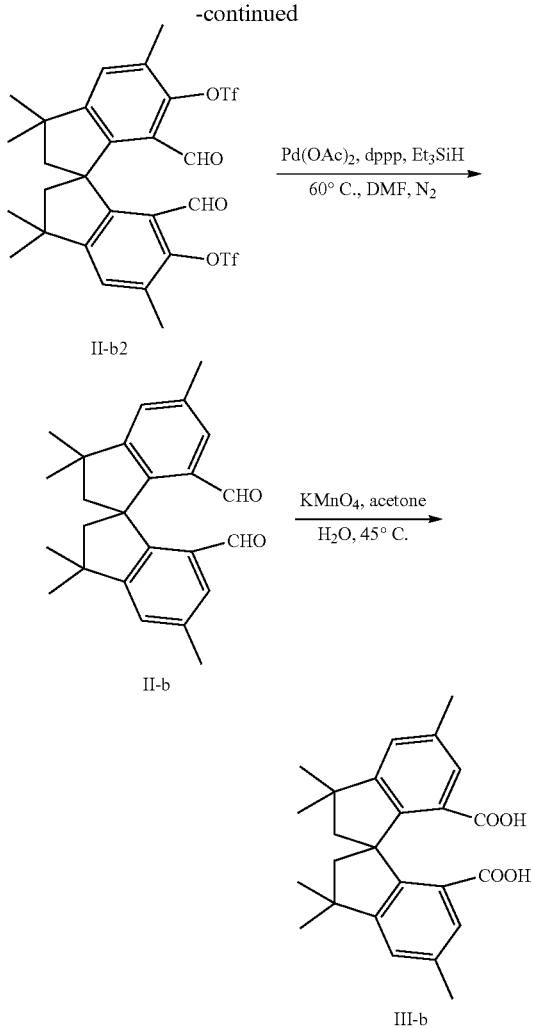

Step 1: 3,3,5,5',3',5'-hexamethyl-1,1'-spirobiindane-6,6'-diol (HMSPINOL, 10 mmol, 3.4 g) and hexamethylenetetramine; (HMTA, 80 mmol, 11.2 g) were added into a. 500 mL three-necked flask under N₂ protection; then, 120 mL of trifluoroacetic acid was added and refluxed overnight; on the next day, 120 mL of glacial acetic acid was added, and the reflux reaction was continued for 3 days; then after cooling to 95° C., 120 mL of hydrochloric acid (4 mol/L) was added, stirred for 5 hours; the reaction was stopped, and the reactants were cooled to room temperature; the reaction solution was poured into water, a large amount of precipitates were precipitated, and a yellow solid product II-b1 was obtained by suction filtration (3.2 g, yield: 82%). m.p. 283.7-285.6° C.; ¹H NMR (400 MHz, CDCl₃) δ 12.01 (s, 2H), 9.57 (s, 2H), 7.20 (s, 2H), 2.57 (d, J=13.5 Hz, 2H), 2.38 (d, J=13.5 Hz, 2H), 2.26 (s, 6H), 1.37 (s, 6H), 1.35 (s, 6H).

Step 2: II-b1 (5 mmol, 1.97 g) was added into a 100 mL three-necked flask under N₂ protection; 40 mL of methylene chloride and pyridine (40 mmol, 3.3 mL) were added, cooled to below 0° C. in ice bath, and trifluoromethanesulfonic anhydride (20 mmol, 3.4 mL) was added dropwise; after addition, the reaction solution was naturally raised to room temperature and stirred overnight, and the reaction was completely monitored by TLC; the reaction solution was poured into a separatory funnel, washed with a 5% HCl solution, a saturated saline solution, a saturated NaH CO₃ solution and a saturated saline solution successively and dried with anhydrous Na₂SO₄; after removing the solvent, a proper amount of dichloroethane, was used for dissolution, and silica gel column chromatography (ethyl acetate/petroleum ether=1/50) was performed quickly to obtain a white solid product II-b2 (3.1 g, yield 95%). m.p. 155.4-157.2° C.; ¹H NMR (400 MHz, CDCl₃) δ9.79 (s, 2H), 7.35 (s, 2H), 2.51 (d, J=12.8 Hz, 2H), 2.45 (s, 6H), 2.42 (d, J=12.8 Hz, 2H), 1.50 (s, 6H), 1.40 (s, 6H).

Step 3: II-b2 (3 mmol, 1.97 g), palladium acetate (0.6 mmol, 135 mg) and 1,3-bis (diphenylphosphine) propane (0.6 mmol, 248 mg) were added into a 250 mL three-necked flask tinder N₂ protection; 150 mL of n, n-dimethylformamide (DMF) was added to obtain a clear solution, and triethylsilane (45 mmol, 7.2 mL) was slowly added dropwise; after the addition, the reaction solution was heated to 60° C. and reacted for 6 hours; TLC monitoring showed that the reaction was complete; the reaction temperature was adjusted back to room temperature, ether was added to dilute the reaction solution, and then the reaction solution was washed with water, a saturated NaH CO₃ solution and a saturated saline solution successively and dried with anhydrous Na₂SO₄; after solvent removal and flash column chromatography (ethyl acetate/petroleum ether=1/15), yellow solid 3,3,5,5',3',5'-hexamethyl-1,1'-spirobiindane-7,7'-dicarboxaldehyde (II-b) (950 mg, yield 88%) was obtained. m.p. 173.6-175.9° C.; ¹H NMR (400 MHz, CDCl₃) δ9.56 (s, 2H), 7.53 (s, 2H), 7.25 (s, 2H), 2.56 (d, J=13.3 Hz, 2H), 2.43 (d, J=17.1 Hz, 8H), 1.45 (s, 61H), 1.40 (s, 61H).

Step 4: II-b (2.5 mmol, 900 mg) was added into a 250 mL round bottom flask, 80 mL of acetone was added, and dissolved completely; a mixed solution of water (20 mL) and acetone (80 mL) in which KMnO₄ (15 mmol, 2.37 g) was dissolved was added into the reaction solution; the reaction was raised to 45° C. for overnight, and TLC monitoring showed that the reaction was complete; the reaction temperature was adjusted back to room temperature, 4M of a NaOH solution was added to the system until the pH value of the reaction solution was 10-11, suction filtration was carried out, acetone was spin-dried, the water phase was washed with petroleum ether for three times, 4 M of a HCl solution was added to the water phase until the pH value was 2, and a large number of white solids were precipitated; extraction was performed with ethyl acetate for three times, organic phases were combined, dried with anhydrous Na₂SO₄, and spin-dried to obtain white solid product 3,3,5,3',3',5'-hexamethyl-1,1'-spirobiindane-7,7'-dicarboxylic acid (III-b) (950 mg, yield 97%). m.p. 317.5-319.2° C.; ¹H NMR (400 MHz, DMSO) δ12.06 (s, 2H), 7.26 (s, 2H), 7.12 (s, 2H), 2.74 (d, J=12.1 Hz, 2H), 2.29 (s, 6H), 2.18 (d, J=12.1 Hz, 2H), 1.37 (s, 6H), 1.35 (s, 6H).

Example 2

Synthesis of (S)-3,3,5,3',3',5'-hexamethyl-1,1'-spirobiindane-7,7'-dicarboxaldehyde ((S)-II-b) and (S)-3,3,5,3',3',5'-hexamethyl-1,1'-spirobiindane-7'7-dicarboxylic Acid ((S)-III-b)

According to the process of Example 1, chiral (S)-3,3,5,3',3',5'-hexamethyl-1,1'-spirobiindane-6,6'-diol ((S)-HMSPINOL) was used to replace 3,3,5,3',3',5'-hexamethyl-1,1'-spirobiindane-6,6'-diol (HMSPINOL) to prepare corresponding (S)-3,3,5,3',3',5'-hexamethyl-1,1'-spirobiindane-7,7'-dicarboxaldehyde ((S)-II-b), yield 65%) and (S)-

3,3,5,3',3',5'-hexamethyl-1,1'-spirobiindane-7,7-dicarboxylic acid ((S)-III-b), yield 60%).

Example 3

Synthesis of 3,3,3',3'-tetramethyl-1,1'-spirobiindane-6,6'-dyhydroxyl-7,7'-dicarboxaldehyde (II-c)

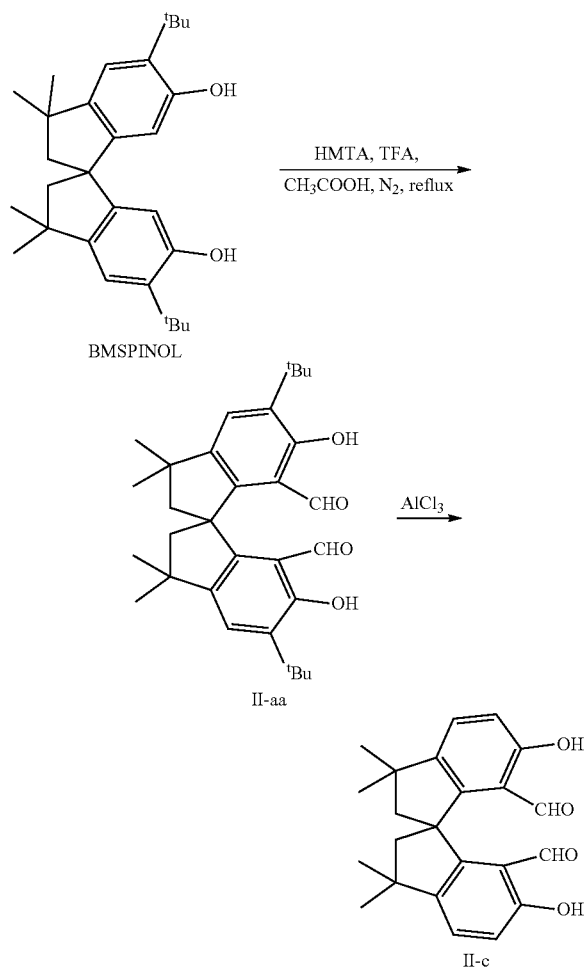

5.2 g of the compound (BMSPINOL, 12.4 mmol) and 10.8 g of hexamethylenetetramine (HMTA, 77 mmol) were added into a reaction flask under nitrogen protection; 150 mL of trifluoroacetic acid (TFA) was added, and the reaction solution was heated for reflux reaction overnight, then 150 mL of acetic acid added, the reflux reaction was continued for 72 hours; 200 mL of 6 mol/L hydrochloric acid was added, and the reaction solution was stirred for reflux hydrolysis for 28 hours; 100 mL of water was added, and the reaction solution was stirred for reaction for 24 hours, and then the reaction solution was cooled, suction-filtered and the filter cake was fully washed with water, and dried to obtain 4.6 g yellow powdery solid product JI-aa with a yield of 80% The melting point was 226-227° C. $^1$H NMR (400 MHz, CDCl$_3$) δ 12.55 (s, 2H), 9.60 (s, 2H), 7.30 (s, 2H), 2.56 (d, J=13.5 Hz, 2H), 2.39 (d, J=135 Hz, 2H), 1.42 (s, 18H), 1.37 (s, 6H), 1.35 (s, 6H).

2 g of the compound II-aa (4.2 mmol) and 10 g of anhydrous aluminum chloride (75 mmol) were added into the reaction flask under nitrogen protection, 30 mL of toluene was added, and 20 mL of nitromethane was added in ice bath; the reaction solution was stirred for reaction overnight at room temperature; the progress of the reaction was monitored by a TLC plate; after the reaction was completed, 3 mol/L hydrochloric acid was slowly added in ice bath to quench the reaction, and the reaction solution was stirred for reaction overnight; ethyl acetate was added for extraction, the organic phase was washed with water and saturated sodium chloride in turn, dried with anhydrous sodium sulfate, and desolventized; the residue was subjected to flash column chromatography with dichloromethane to obtain 1.2 g of light yellow powdery solid 3,3,3',3'-tetramethyl-1,1'-spirobiindane-6,6-dyhydroxyl-7,7-dicarboxaldehyde (II-c) with a yield of 78%. The melting point was 219-220° C. $^1$H NMR (400 MHz, CDCl$_3$) δ 11.72 (s, 2H), 9.58 (s, 2H), 7.35 (d, J=8.6 Hz, 2H), 6.94 (d, J=8.6 Hz, 2H), 2.62 (d, J 13.5 Hz, 2H), 2.43 (d, J=13.5 Hz, 2H), 1.37 (s, 6H), 1.35 (s, 6H).

Example 4

Synthesis of (R)-3,3,3',3'-tetramethyl-1,1'-spirobiindane-6,6'-dyhydroxyl-7,7'-dicarboxaldehyde ((R)-II-c)

According to the process of Example 3, chiral (R)-BMSPINOL was used to replace racemate compound BMSPINOL to prepare the corresponding (R)-3,3,3',3'-tetramethyl-1,1'-spirobiindane-6,6'-dyhydroxyl-7,7'-dicarboxaldehyde ((R)-II-c, with a total yield of 64%).

Example 5

Synthesis of 3,3,3',3'-tetramethyl-1,1'-spirobiindane-7,7'-dicarboxaldehyde (II-a) and 3,3,3,3-tetramethyl-1,1'-spirobiindane-7,7'-dicarboxylic acid (III-b)

According to the reaction process from step 2 to step 4 in Example 1, 3,3,3',3'-tetramethyl-1,1'-spirobiindane-6,6'-dyhydroxyl-7,7-dicarboxaldehyde (II-c) was used to replace 3,3,5,3',3',5'-hexamethyl-1,1'-spirobiindane-6,6'-dyhydroxyl-7,7'-dicarboxaldehyde (II-b1) in step 2, and the feeding materials in step 3 and step 4 were changed correspondingly to prepare the corresponding 3,3,3',3'-tetramethyl-1,1-spirobiindane-7,7'-dicarboxaldehyde (II-a, with a total yield of 85%) and 3,3,3',3'-tetramethyl-1,1'-spirobiindane-7,7'-dicarboxylic acid (III-b, with a total yield of 82%).

According to the same process, chiral (R)-II-a (a total yield of 86%) and (R)-III-a (a total yield of 84%) were obtained by using chiral (R)-II-c as a raw material.

Example 6

Synthesis of 3,3,3',3'-tetramethyl-1,1'-spirobiindane-6,6'-dimethoxy-7,7'-dicarboxaldehyde (II-d)

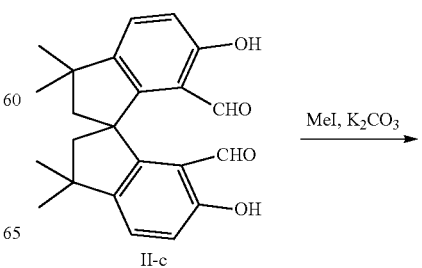

-continued

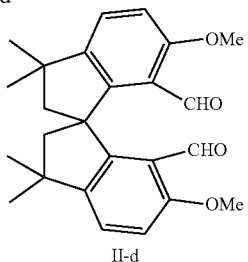

II-d 3 g of II-c and 4 g of potassium carbonate were added into the reaction flask, 50 mL of acetone was added, 2 mL of methyl iodide was poured into the reaction solution, which was then stirred and refluxed for 12 hours until the raw materials disappeared and become a product point by as monitored by TLC; 60 mL of concentrated ammonia water was added, and stirring was continued for 2 hours; after cooling to room temperature, suction filtration was carried out, the filtration cake was washed with hot water for 3 times and dried to obtain white powder II-d with a yield of 950%.

Example 7

Synthesis of 3,3,3',3'-tetramethyl-1,1'-spirobiindane-6,6'-diphenyl-7,7'-dicarboxaldehyde (II-e)

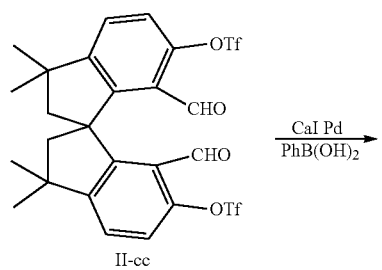

II-cc

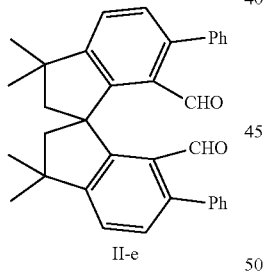

II-e

Under nitrogen protection II-cc (0.2 g), phenylboronic acid (0.38 g), potassium bromide (0.1 g) and tetrakis (triphenylphosphine) palladium (60 mg) were added into a reaction flask, and then 2 mL of dimethoxyethane (DME), 1 mL of water and 0.45 g of potassium phosphate tribasic trihydrate were added to react with stirring at 90° C. for 24 hours, and TLC monitoring was carried out until the reaction ended; then water was added to quench the reaction; extraction was carried out with ethyl acetate, followed by drying with anhydrous sodium sulfate and suction filtration; and then the filtrate was concentrated to dry, and flash silica gel column chromatography was carried out to obtain powdery solid II-e with a yield of 60%. $^1$H NMR (400 MHz, CDCl$_3$) δ 9.50 (s, 2H), 7.45 (d, J=7.8 Hz, 2H), 7.36-7.20 (m, 12H), 2.74 (d, J=12.5 Hz, 2H) 2.47 (d, J=12.5 Hz, 2H), 1.58 (s, 61H), 1.47 (s, 6H).

Example 8

Synthesis of 3,3,5,3',3',5'-hexamethyl-1,1'-spirobiindane-7,7'-bisoxazoline

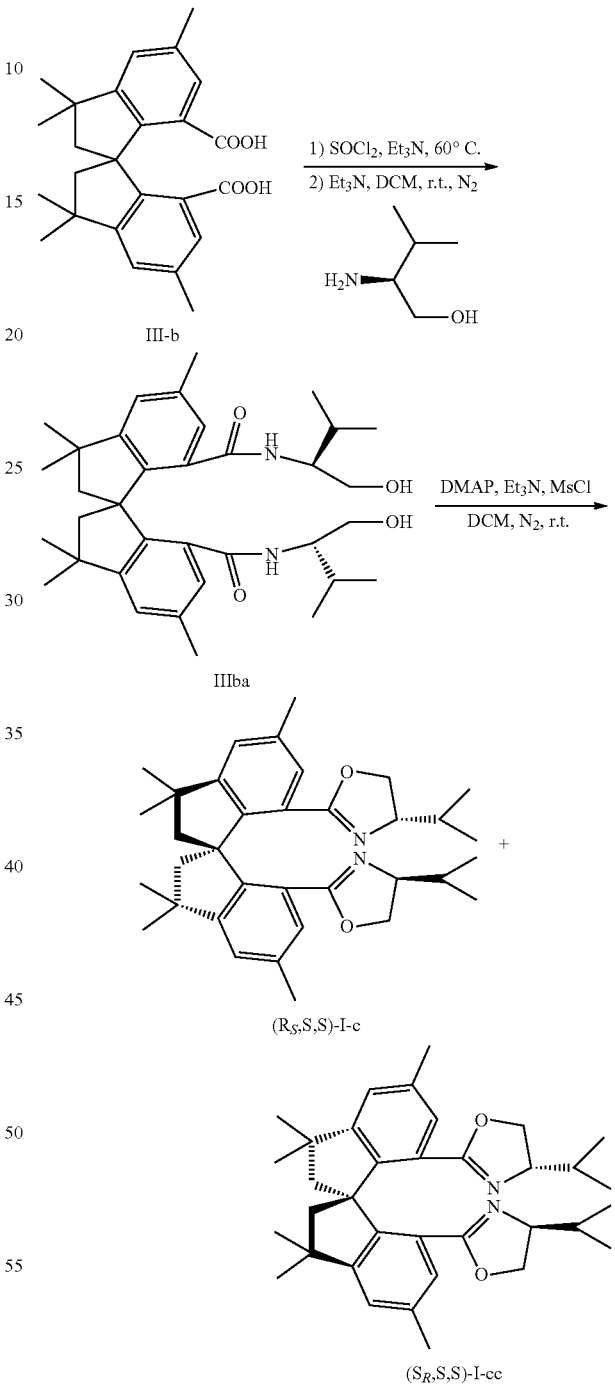

Hexamethyl spirocyclodicarboxylic acid III-b (5 mmol, 1.97 g) Was added into the reaction flask, and 60 mL of thionyl chloride was added, stirred and dissolved; then triethylamine (20 mmol, 2.78 mL) was added dropwise, after which the reaction was heated to 60° C. and stirred for 3 hours; rotary evaporation was carried out under reduced pressure to remove volatiles to obtain acyl chloride; under N$_2$ protection, 50 mL of a dichloromethane was added to dissolve the acyl chloride; the reaction solution was cooled to 0° C. in an ice bath, and then triethylamine (20 mmol, 2.78 mL) and L-valinol (20 mmol, 2.07 g) in dichloromethane (10 mL) were added in turn; after the addition, they were heated to room temperature and reacted overnight, and the reaction was complete by TLC monitoring; water was added to quench the reaction, extracting was carried out with dichloromethane, followed by drying with Na$_2$SO$_4$ and drying by desolventization, thereby obtaining the product of amide alcohol IIIba for the next step.

Amide alcohol IIIba (5 mmol) and 4-dimethylaminopyridine (DMAP, 1 mmol, 122 mg) were added into the reaction flask under N$_2$ protection; 75 mL of dichloromethane was added and stirred to dissolve; after cooling to 0° C. in ice water bath, triethylamine (40 mmol, 5.7 mL) and methanesulfonyl chloride (MsCl, 20 mmol, 1.6 mL) were added in turn; after the addition, the system was naturally heated to room temperature and reacted overnight; TLC monitoring showed that the reaction was complete; the reaction was quenched with water, extraction was carried out with dichloromethane, followed by washing with saturated salt water and drying with anhydrous Na$_2$SO$_4$; a pair of diastereoisomers (R$_a$, S, S)-I-c (1.1 g, with a field of 84%) and (S$_a$, S, S)-I-cc (10.06 g, with a field of 81%) were obtained by rotary desolvation under reduced pressure and silica gel column chromatography (ethyl acetate/petroleum ether=1/15-1/4).

(R$_a$, S, S)-I-c: m.p. 66.2-68.0° C.; $[\alpha]_D^{20}$=+93 (c 0.12, CH$_2$Cl$_2$); $^1$H NMR (400 MHz, CDCl$_3$) δ7.34 (s, 2H), 7.03 (d, J=0.9 Hz, 2H), 3.76 (dd, J=9.6, 8.1 Hz, 2H), 3.44 (td, J=9.4, 7.2 Hz, 2H), 2.95-2.88 (m, 2H), 2.84 (d, J=12.2 Hz, 2H), 2.32 (s, 6H), 2.27 (d, J=12.2 Hz, 2H), 1.45 (dq, J=13.6, 6.8 Hz, 2H), 1.36 (s, 121H), 0.87 (d, J=6.7 Hz, 61H), 0.66 (d, J=6.8 Hz, 6H);

(S$_a$, S, S)-I-cc: $[\alpha]_D^{20}$=−173 (c 0.15, CH$_2$Cl$_2$); $^1$H NMR, (400 MHz, CDCl$_3$) δ7.51 (s, 2H), 7.07 (d, J=0.8 Hz, 2H), 3.67 (dt, J=9.7, 5.7 Hz, 2H), 3.60 (dd, J=7.9, 6.2 Hz, 2H), 2.89 (dd, J=9.6, 8.1 Hz, 2H), 2.67 (d, J=12.2 Hz, 2H), 2.35 (s, 6H), 2.29 (d, J=12.2 Hz, 2H), 1.65 (dq, J=13.4, 6.7 Hz, 2H), 1.35 (s, 6H), 1.37 (s, 6H), 0.81 (d, J=6.8 Hz, 6H), 0.73 (d, J=6.8 Hz, 6H).

According to the above processes, the following bisoxazoline ligand compound and its characterization can be obtained:

[(R$_a$, S, S)-I-Ph]:

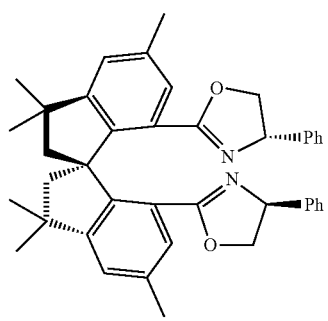

1.35 g, 91% yield (two steps); white solid, m.p. 171-172° C.; $[\alpha]_D^{20}$=−47 (c 0.12, CH$_2$Cl$_2$); $^1$H NMR (400 MHz, CDCl$_3$) δ7.48 (d, J=0.7 Hz, 2H), 7.26 (dd, J=8.3, 6.0 Hz, 4H), 7.23-7.13 (m, 6H), 7.01 (d, J=0.8 Hz, 2H), 4.72 (t, J=10.2 Hz, 2H), 4.21 (dd, J=10.0, 8.2 Hz, 2H), 3.06 (dd, J=10.3, 8.2 Hz, 2H), 2.99 (d, J=12.1 Hz, 2H), 2.32 (d, J=12.1 Hz, 2H), 2.21 (s, 6H), 1.38 (s, 6H), 1.32 (s, 6H);

Monocrystal data (as shown in FIG. 1): Cell: a=8.0415(4) b=9.7317(5) c=41.5986(18); alpha=90 beta=90 gamma=90: Temperature: 130 K; Volume 3255.4(3) Space group P 21 21 21; Hall group P 2ac 2ab;

[(S$_a$, S, S)-I-Ph]:

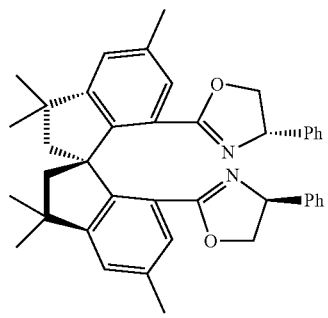

1.29 g 87% yield (two steps); white solid, m.p. 101-102° C.; $[\alpha]_D^{20}$=−94 (c 0.13, CH$_2$Cl$_2$); $^1$H NMR (400 MHz, CDCl$_3$) δ7.58 (s, 2H), 7.16 (dt, J=14.3, 7.8 Hz, 61H), 7.02 (d, J=8.7 Hz, 6H), 4.82 (dd, J=10.1, 6.1 Hz, 2H), 3.71 (dd, J=7.9, 6.3 Hz, 2H), 3.18 (dd, J=10.0, 8.3 Hz, 2H), 2.67 (d, J=12.3 Hz, 2H), 2.32 (s, 6H), 2.28 (d, J=12.3 Hz, 2H), 1.35 (s, 6H), 1.23 (s, 6H);

[(R$_a$, S, S)-I-d]:

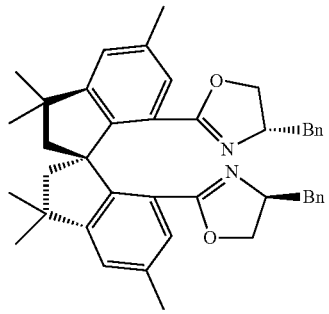

1.31 g 84% yield (two steps); white solid, m.p. 57-58° C.; $[\alpha]_D^{20}$=+51 (c 0.15, CH$_2$Cl$_2$); $^1$H NMR (400 MHz, CDCl3) δ7.50 (s, 2H), 7.25 (dd, J=9.0, 5.5 Hz, 4H), 7.18 (t, J=7.3 Hz, 2H), 7.08 (dd, J=10.7, 4.0 Hz, 6H), 4.04 (qd, J=9.2, 4.8 Hz, 2H), 3.76 (t, J=8.7 Hz, 2H), 3.10 (dd, J=13.6, 4.7 Hz, 2H), 2.79 (dd, J=14.2, 5.5 Hz, 4H), 2.42 (s, 6H), 2.28 (dd, J=14.3, 11.1 Hz, 4H), 1.40 (s, 6H), 1.32 (s, 6H);

[(S$_a$, S, S)-I-d]:

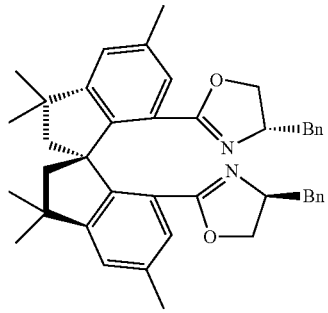

1.26 g, 81% yield (two steps); white solid, m.p. 43-44° C.; [α]$_D^{20}$=−24 (c 0.19, CH$_2$Cl$_2$); $^1$H NMR (400 MHz, CDCl$_3$) δ. 7.43 (s, 2H), 7.29-7.22 (m, 6H), 7.18 (t, J=7.3 Hz, 2H), 7.09 (d, J=7.0 Hz, 4H), 7.03 (d, J=0.9 Hz, 2H), 4.28-3.96 (m, 2H), 3.57 (dd, J=8.2, 6.2 Hz, 2H), 3.02 (t, J=8.8 Hz, 2H), 2.91 (dd, J=13.8, 4.0 Hz, 2H), 2.75 (d, J=12.2 Hz, 2H), 2.33 (s, 6H), 2.29 (d, J=12.2 Hz, 2H), 2.08 (dd, J=13.7, 10.5 Hz, 2H), 1.38 (s, 6H), 1.34 (s, 6H);

[(R$_a$, 4S, 4'S, 5S, 5'S)-I-DPh]:

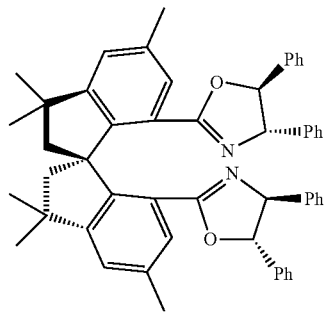

1.42 g, 76% yield (two steps); white solid, m.p. 196-197° C.; [α]$_D^{20}$=−97 (c 0.10, CH$_2$Cl$_2$); $^1$H NMR (400 MHz, CDCl$_3$) δ7.69 (s, 2H), 7.30 (dd, J=10.8, 5.1 Hz, 6H), 7.24-7.08 (m, 14H), 6.95 (s, 2H), 4.64 (d, J=10.3 Hz, 2H), 4.08 (d, J=10.3 Hz, 2H), 2.97 (d, J=12.0 Hz, 2H), 2.27 (d, J=12.0 Hz, 2H), 2.18 (s, 6H), 1.30 (s, 6H), 0.91 (s, 6H);

[(S$_a$, 4S, 4'S, 5S, 5'S)-I-DPh]:

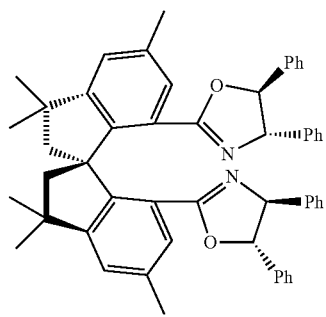

1.38, 74% yield (two steps); white solid, m.p. 52-53° C.; [α]$_D^{20}$=+8 (c 0.12, CH$_2$Cl$_2$); $^1$H NMR (400 MHz, CDCl$_3$) δ7.51 (d, J=1.0 Hz, 2H), 7.31-7.27 (m, 6H), 7.25-7.19 (m, 6H), 7.10-6.99 (m, 4H), 6.94-6.87 (m, 4H), 6.80 (d, J=1.1 Hz, 2H), 4.90 (d, J=9.0 Hz, 2H), 4.75 (d, J=9.0 Hz, 2H), 2.64 (d, J=12.6 Hz, 2H), 2.29 (d, J=12.5 Hz, 2H), 2.15 (s, 6H), 1.31 (s, 6H), 1.17 (s, 6H);

(S, S)-I-1a: R$_f$=0.7 (Petroleum Ether: Ethyl Acetate=4:1);

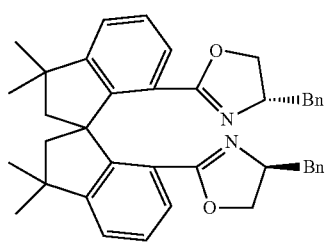 [SMILES: CC1(C)CC2(CC(C)(C)c3cccc(C4=N[C@@H](Cc5ccccc5)CO4)c32)c2c(C3=N[C@@H](Cc4ccccc4)CO3)cccc21]

White solid, m.p. 30.5-31.2° C.; [α]$_D^{20}$=+28 (c 0.10, CH$_2$Cl$_2$); $^1$H NMR (400 MHz, CDCl$_3$) δ7.63 (dd, J=5.9, 3.0 Hz, 2H), 7.34-7.28 (m, 4H), 7.26-7.13 (m, 6H), 7.08 (d, J=7.0 Hz, 4H), 4.08-3.89 (m, 2H), 3.81-3.69 (m, 2H), 3.03 (dd, J=13.7, 5.0 Hz, 2H), 2.86 (dd, J=13.6, 4.9 Hz, 4H), 2.33 (d, J=12.2 Hz, 2H), 2.27 (dd, J=13.7, 9.7 Hz, 2H), 1.42 (s, 6H), 1.35 (s, 6H);

(S, S)-I-1b: R$_f$=0.4 (Petroleum Ether: Ethyl Acetate)

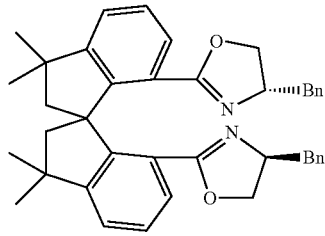 [SMILES: CC1(C)CC2(CC(C)(C)c3cccc(C4=N[C@@H](Cc5ccccc5)CO4)c32)c2c(C3=N[C@@H](Cc4ccccc4)CO3)cccc21]

White solid, m.p. 49.2-50.2° C.; [α]$_D^{20}$=−105 (c 0.11, CH$_2$Cl$_2$); $^1$H NMR (400 MHz, CDCl$_3$) δ7.60 (dd, J=7.2, 1.6 Hz, 2H), 7.26-7.13 (m, 10H), 7.08 (d, J=7.0 Hz, 4H), 4.26-4.01 (m, 2H), 3.57 (dd, J=8.3, 6.2 Hz, 2H), 3.04 (t, J=8.8 Hz, 2H), 2.86 (dd, J=13.8, 4.1 Hz, 2H), 2.79 (d, J=12.2 Hz, 2H), 2.32 (d, J=12.2 Hz, 2H), 2.16-1.98 (m, 2H), 1.41 (s, 6H), 1.37 (s, 6H);

Example 9

Preparation of 3,3,5,3',3',5'-hexamethyl-1,1'-spirobi-indane-7,7'-bisoxazolin from Chiral Hexamethyl Spirocyclodicarboxylic Acid

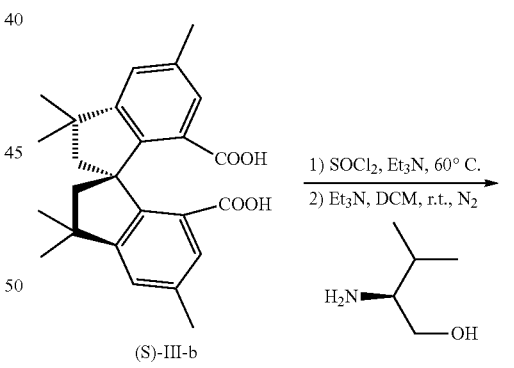

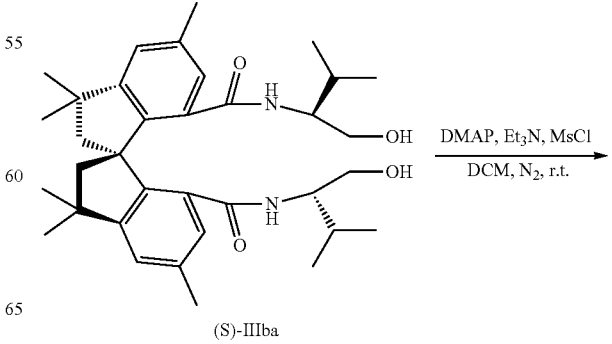

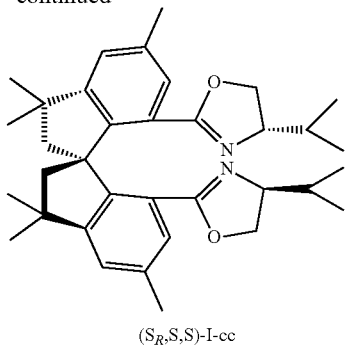

(S$_R$,S,S)-I-cc (S)-3,3,5,3,3',5'''-hexamethyl-1,1'-spirobiindane-7,7'-dicarboxylic acid ((S)-II-b) (5 mmol, 1.97 g) was added into a reaction flask; 60 mL of thionyl chloride was added, stirred and dissolved; and then triethylamine (20 mmol, 2.78 mL) was added dropwise, after which the reaction solution was heated to 60° C. and stirred for 3 hours; rotary evaporation under reduced pressure was carried out to remove volatiles to obtain acyl chloride; under the protection of $N_2$, 60 mL of dichloromethane was added to dissolve the acyl chloride, and the reaction solution was cooled to 0° C. in ice bath; then triethylamine (20 mmol, 2.78 mL) and L-valinol (20 mmol, 2.07 g) in dichloromethane (15 mL) were added in turn; after the addition, the reaction solution was heated to room temperature for reaction overnight; TLC monitoring showed that the reaction was completed; water was added to quench the reaction, extraction was carried out with dichloromethane, followed by drying with $Na_2SO_4$ and desolventization to dryness to obtain the product amide alcohol (S)-IIIba for the next step.

Amide alcohol (S)-IIIba (5 mmol) and 4-dimethylaminopyridine (DMAP, 1 mmol, 122 mg) were added into the reaction flask under $N_2$ protection; 80 mL of dichloromethane was added and stirred for dissolution; after cooling to 0° C. in ice water bath, triethylamine (40 mmol, 5.7 mL) and methanesulfonyl chloride (MsCl, 20 mmol, 1.6 mL) were added in turn, after which, the system was naturally heated to room temperature and reacted overnight; TLC monitoring showed that the reaction was complete; water was added for quenching, extraction was carried out with dichloromethane, followed by washing with saturated salt water and drying with anhydrous $Na_2SO_4$. (S$_a$, S, S)-I-cc (yield: 91%) was obtained by rotary desolvation under reduced pressure and silica gel column chromatography (ethyl acetate/petroleum ether=1/6).

Example 10

Application of Asymmetric Intramolecular Cyclopropanation:

$FeCl_2$·$4H_2O$ (2.0 mg, 0.01 mmol), a ligand (R$_a$, S, S)-I-Ph (7.1 mg, 0.012 mmol), an additive NaBAr$_F$ (10.6 mg, 0.012 mmol) were added into a Schlenk tube under $N_2$ protection; a solvent $CHCl_3$ (1.5 mL) was added, and stirred at room temperature for 4 hours for coordination; then a $CHCl_3$ solution (0.5 mL) of α-diazoester derivative 8 (0.1 mmol) was added into the reaction solution, the temperature was raised to 60° C., and reaction was continued for 24 hours; the completion of the reaction was monitored by TLC; the reaction was stopped and cooled to room temperature, the reaction solution was concentrated, and was subjected to perform silica gel column chromatography (ethyl acetate/petroleum ether=1/10) to obtain a chiral cyclopropanation product 9.

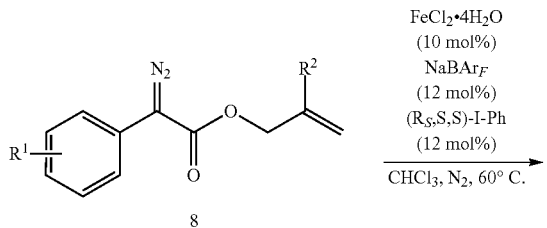

The results of the reaction are as below:

(1S,5S)-1-(4-chlorophenyl)-5-methyl-3-oxabicyclo[3.1.0]hexan-2-one (9a)

21 mg, 93% yield; white solid; m.p. 122-123° C.; 92% ee; HPLC analysis: Chiralpak OJ-H (hexane/i-PrOH=80/20, 1.0 mL/min, 210 nm), t$_R$ (major) 18.115 min, t$_R$ (minor) 21.659 min; [α]$_D^{20}$=+49 (c 0.04, $CH_2Cl_2$); $^1$H NMR (400 MHz, $CDCl_3$) δ7.39-7.32 (m, 2H), 7.23-7.16 (n, 2H), 4.36 (d, J=9.2 Hz, 1H), 4.19 (d, J=9.2 Hz, 1H), 1.58 (d, J=5.0 Hz, 1H), 1.41 (d, J=5.0 Hz, 1H), 1.17 (s, 3H);

Comparative example: the ligand 1,1'-spirobiindane-7,7'-bis(phenyloxazoline) (R$_a$, S, S)-SpiroBOX-Ph known in the literatures was used to replace the ligand (R$_a$, S, S)-I-Ph in the same reaction process to obtain a product 9a with an optical purity of less than 80% ee.

(1S, 5S)-1-(3-chlorophenyl)-5-methyl-3-oxabicyclo[3.1.0]hexan-2-one (9b)

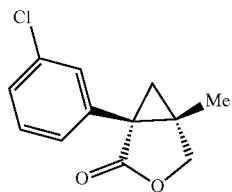 [SMILES: C[C@@]12COC(=O)[C@]1(c1cccc(Cl)c1)C2]

21 mg. 93% yield; white solid; m.p. 67-68° C.; 96% ee; HPLC analysis: Chiralpak AS-H (hexane/i-PrOH=80/20, 1.0 mL/min, 210 nm), $t_R$ (major) 12.981 min, $t_R$ (minor) 19.715 min; $[\alpha]_D^{20}$=+75 (c 0.07, CH$_2$Cl$_2$); $^1$H-NMR (400 MHz, CDCl$_3$) δ7.24 (dd, J=3.9, 1.3 Hz, 2H), 7.19 (dd, J=3.3, 18 Hz, 1H), 7.13-7.03 (m, 1H), 4.29 (d, J=9.2 Hz, 1H), 4.12 (d, J=9.2 Hz, 1H), 1.54 (d, J=5.0 Hz, 1H), 1.35 (d, J=5.0 Hz, 1H) 1.11 (s, 3H);

(1R,5S)-1-(2-chlorophenyl)-5-methyl-3-oxabicyclo[3.1.0]hexan-2-one (9c)

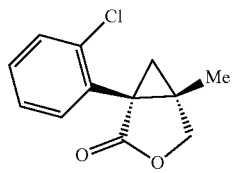 [SMILES: C[C@@]12COC(=O)[C@]1(c1ccccc1Cl)C2]

22 mg, 96% yield; white solid; m.p. 120-121° C.; 95% ee; HPLC analysis: Chiralpak AS-H (hexane/i-PrOH=80/20, 1.0 mL/min, 210 nm), $t_R$ (major) 13.977 min, $t_R$ (minor) 16.589 min; $[\alpha]_D^{20}$=+3 (c 0.05, CH$_2$Cl$_2$); $^1$H NMR (400 MHz, CDCl$_3$) δ 7.42-7.31 (m, 1H), 7.28-7.18 (m, 3H), 4.31 (dd, J=27.4, 9.0 Hz, 2H), 1.45 (d, J=5.0 Hz, 1H), 1.36 (d, J=5.0 Hz, 1H), 1.08 (s, 3H).

Example 11

Application in Forming a Complex with a Metal Salt:

FeCl$_2$.4H$_2$O (2.0 mg, 0.01 mmol) and a ligand (R$_a$, S, S)-I-Ph (0.01 mmol) were added into a Schlenk tube under N$_2$ protection; a solvent CHCl$^3$ (2 mL) was added and stirred at room temperature for 4 hours; the reaction solution was concentrated under reduced pressure, and subjected to vacuum draining to quantitatively obtain a complex [(R$_a$, S, S)-I-Ph]FeCl$_2$; Cu(OTf)$_2$ (0.01 mmol) and a ligand (R$_a$, S, S)-I-Ph (0.01 mmol) were added into a Schlenk tube under N$_2$ protection; a solvent CHCl$_3$ (2 mL) was added and stirred for coordination at room temperature for 4 hours; the reaction solution was concentrated under reduced pressure, and then subjected to vacuum draining to obtain a complex [(R$_a$, S, S)-I-Ph]Cu(OTf)$_2$.

Example 12

Application of Asymmetric Intermolecular Si—H Insertion Reaction:

Fe(OTf)$_2$ (1.77 mg, 0.005 mmol), a ligand (R$_a$, S, S)-I-Ph (3.6 mg, 0.006 mmol), an additive NaBAr$_F$ (5.3 mg, 0.006 mmol) were added into a Schlenk tube under N$_2$ protection; a solvent CH$_2$Cl$_2$ (1.5 mL) was added and stirred for coordination for 4 hours at room temperature; then diazo ester derivative 10 (0.1 mmol) in CH$_2$Cl$_2$ solution (0.5 mL) was added to the reaction solution, stirred for 30 min, and then triethylsilane (64 μL, 0.4 mmol) was added; the temperature was raised to 40° C. to continue the reaction for 48 hours; TLC monitored the completion of the reaction; the reaction was stopped and cooled to room temperature; the reaction solution was concentrated and subjected to flash silica gel column chromatography (ethyl acetate/petroleum ether:=:1/100) to obtain a product 11 of an asymmetric intermolecular Si—H insertion reaction.

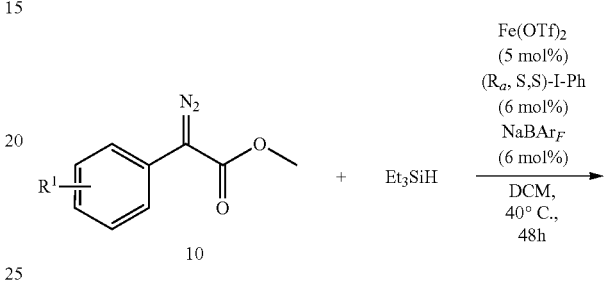

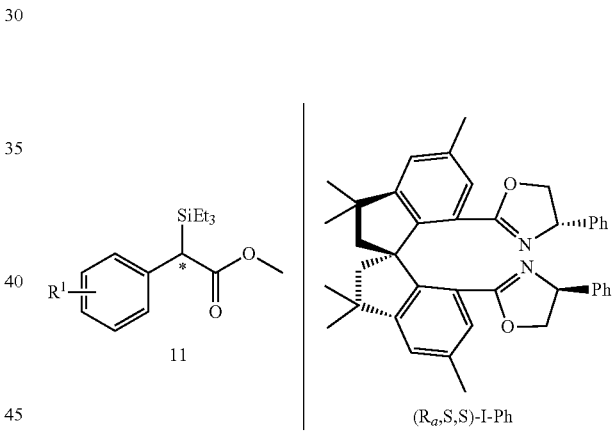

The results of reaction are as below:

Methyl 2-phenyl-2-(triethylsilyl)acetate (11a)

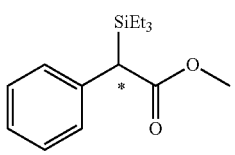

25 mg, 95% yield; colorless oil; 91% ee; HPLC analysis: Chiralpak OD-H (hexane/i-PrOH=99/1, 0.8 mL/Min, 225 nm), t (major) 2.014 min, t (minor) 10.637 min; $^1$H NMR (400 MHz, CDCl$_3$) δ7.36 (dd, J=6.9, 5.5 Hz, 2H), 7.31-7.25 (m, 2H), 7.20-7.13 (m, 1H), 3.67 (s, 31H), 3.53 (s, 1H), 0.90 (dd, J=9.5, 63 Hz, 9H), 0.59 (ddd, J=11.9, 7.9, 3.4 Hz, 6H).

Methyl 2-(4-chlorophenyl)-2-(triethylsilyl)acetate
(11b)

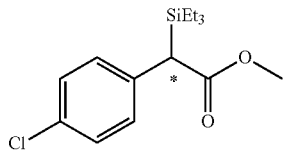

27 mg, 90% yield; colorless oil; 93% ee; HPLC analysis: Chiralpak PA-2 (hexane/i-PrOH=98/2, 0.8 mL/min, 214 nm), t (minor) 5.485 min, t (major) 6.553 min; $^1$H NMR (400 MHz, CDCl$_3$) δ7.31-7.22 (m, 4H), 3.68 (s, 3H), 3.51 (s, 1H), 0.90 (dd, J=9.5, 6.3 Hz, 9H), 0.58 (ddd, J=12.0, 7.9, 3.6 Hz, 6H).

What is claimed is:

1. A 3,3,3',3'-tetramethyl-1,1'-spirobiindane-based bisoxazoline ligand, being a compound represented by formula I, or being an enantiomer, or a diastereomer thereof:

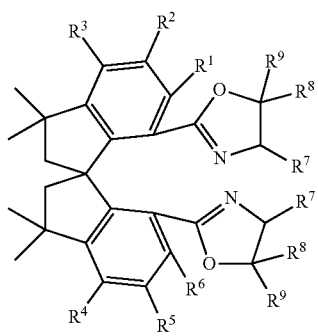

wherein $R^1$ and $R^6$ are each independently selected from the group consisting of hydrogen, $C_1$-$C_{10}$ alkyl, and aryl; $R^2$, $R^3$, $R^4$, and $R^5$ are each independently selected from hydrogen, or $C_1$-$C_{10}$ alkyl; and $R^7$ is selected from the group consisting of hydrogen, $C_1$-$C_{10}$ alkyl, $C_6$-$C_{14}$ aryl, and arylmethylene; $R^8$ and $R^9$ are each independently selected from the group consisting of hydrogen, $C_1$-$C_{10}$ alkyl, and $C_6$-$C_{14}$ aryl.

2. The 3,3,3',3'-tetramethyl-1,1'-spirobiindane-based bisoxazoline ligand according to claim 1, wherein the compound represented by formula I is any one of the following compounds:

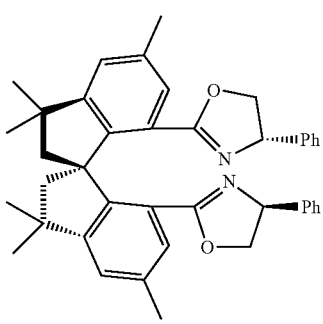

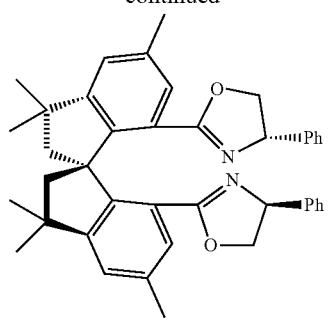

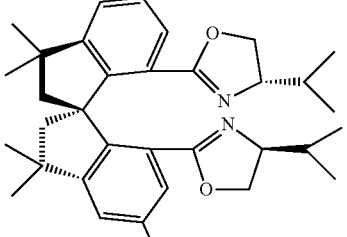

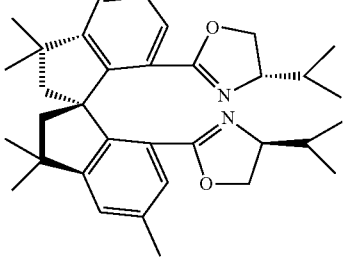

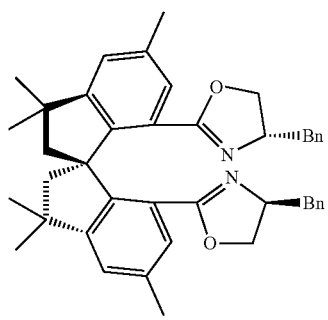

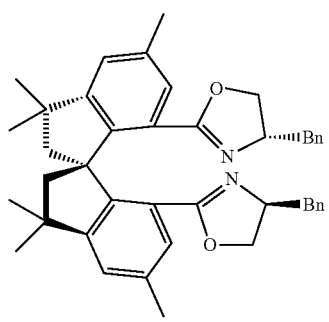

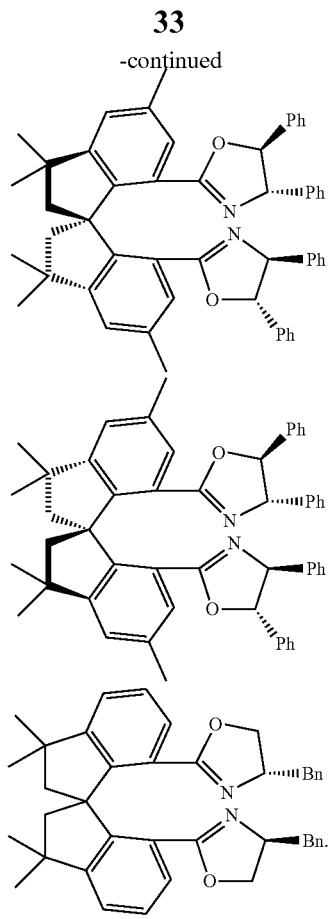

3. A method for preparing the compound of formula I according to claim 1, comprising the following steps of: using the compound of formula II as a starting material, preparing the compound of formula III through a potassium permanganate oxidation reaction, then carrying out an acyl chlorination reaction, condensing with aminoethanol compounds to form amide alcohol, and finally cyclizing to obtain the compound of formula I:

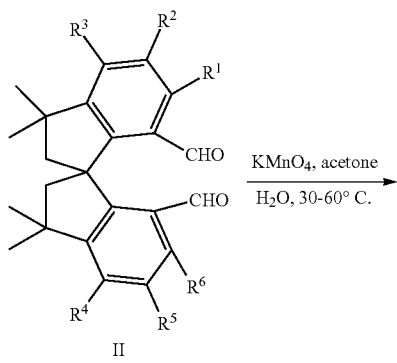

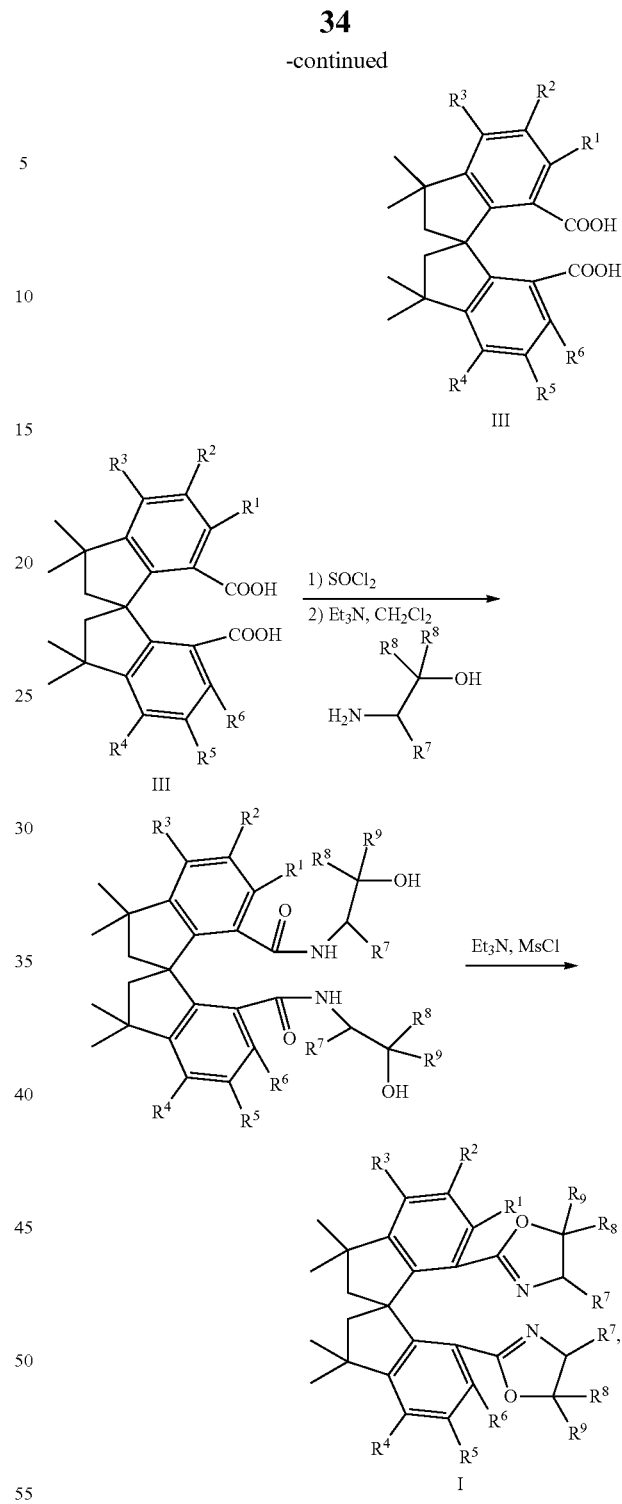

wherein, $R^1$-$R^9$ are the same as those defined in claim 1.

* * * * *